US008569685B2

(12) United States Patent
Finlay

(10) Patent No.: US 8,569,685 B2
(45) Date of Patent: Oct. 29, 2013

(54) PORTABLE ANALYTICAL SYSTEM FOR ON-SITE ANALYSIS OF FLUIDS

(75) Inventor: Alan Finlay, West Byfleet (GB)

(73) Assignee: Microsaic Systems PLC, Woking, Surrey (GB)

( * ) Notice: Subject to any disclaimer, the term of this patent is extended or adjusted under 35 U.S.C. 154(b) by 361 days.

(21) Appl. No.: 12/902,611

(22) Filed: Oct. 12, 2010

(65) Prior Publication Data

US 2011/0084202 A1    Apr. 14, 2011

(30) Foreign Application Priority Data

Oct. 12, 2009   (GB) .................................. 0917758.5

(51) Int. Cl.
   *G01V 5/00*   (2006.01)
   *H01J 49/00*  (2006.01)

(52) U.S. Cl.
   USPC ........................... 250/254; 250/255; 250/288

(58) Field of Classification Search
   USPC .......... 250/254, 255, 256, 257, 259, 287, 288
   See application file for complete search history.

(56) References Cited

U.S. PATENT DOCUMENTS

| 6,670,605 B1 | 12/2003 | Storm, Jr. et al. |
| 7,667,193 B2 | 2/2010 | Finlay |
| 7,786,434 B2 | 8/2010 | Syms |
| 8,215,388 B2 * | 7/2012 | van Zuilekom et al. ...... 166/264 |
| 2005/0082473 A1 * | 4/2005 | Socki et al. .................... 250/288 |
| 2009/0026361 A1 | 1/2009 | Syms |
| 2009/0050369 A1 | 2/2009 | Pop et al. |
| 2009/0090197 A1 | 4/2009 | Finlay |
| 2009/0212210 A1 | 8/2009 | Finlay |

FOREIGN PATENT DOCUMENTS

| GB | 2441069 A | 2/2008 |
| WO | 03/001196 A1 | 1/2003 |
| WO | 2007/085797 A1 | 8/2007 |

OTHER PUBLICATIONS

Great Britain Search Report for Priority Application No. GB0917758.5.

* cited by examiner

*Primary Examiner* — David Porta
*Assistant Examiner* — Faye Boosalis
(74) *Attorney, Agent, or Firm* — Bishop Diehl & Lee, Ltd.

(57) ABSTRACT

A portable analytical system for the rapid on-site analysis of fluids, and a method for using this system at the well-site for the analysis of samples extracted from drilling fluids is described. The portable analytical solution may be deployed at the well-site and used to perform detailed real-time analysis of formation fluids and extracts of rock cuttings. The method described could be used during hydrocarbon exploration and production to determine whether the drill stem has passed through a hydrocarbon-bearing region, or rocks that are capable of functioning as an oil reservoir or that may have been a source rock, or that may have come into contact with oil, or that may contain oil at present.

14 Claims, 10 Drawing Sheets

PORTABLE ANALYTICAL SYSTEM FOR ON-SITE ANALYSIS OF FLUIDS

CROSS-REFERENCE TO RELATED APPLICATIONS

This application claims the benefit of United Kingdom Patent Application Serial No. 0917758.5 filed on Oct. 12, 2009.

TECHNICAL FIELD OF THE INVENTION

The present invention relates to on-site fluid analysis and in particular to a portable analytical system for the rapid on-site analysis of fluids, and a method for using this system 'topside' at a well-site for the analysis of samples extracted from drilling fluids. The invention more particularly relates to an apparatus and methodology that may be used in analysis of drilling fluids which have been returned to the surface, or topside, at the well-site location. In such an environment, the portable analytical solution may deployed at the well-site and used to perform detailed real-time analysis of formation fluids and extracts of rock cuttings for use during oil and gas exploration and production to determine whether the drill stem has passed through a hydrocarbon-bearing region, or rocks that are capable of functioning as an oil reservoir or that may have been a source rock, or that may have come into contact with oil, or that may contain oil at present.

BACKGROUND OF THE INVENTION

Producible accumulations of hydrocarbon reserves occur when hydrocarbons generated from source rock migrate through the subterranean to a trap where they are accumulated. Reservoir rock that once contained high oil saturation is generally referred to as a 'paleo oil zone' and traces of remaining oil are known as 'oil shows' or 'residual oil'. Paleo oil zones sometimes indicate proximity to oil accumulations. Detecting current oil zones or paleo oil zones while drilling can aid decision making. For example, detecting a paleo zone may prompt additional testing that would not have been made without detection. If paleo zones can be detected quickly a well could be drilled to locate a current oil accumulation in proximity to the first drill site.

Existing techniques that detect paleo oil zones may also detect current oil zones. Also, detection of oil accumulation and migration in the geological past is critical for the evaluation of wells during exploration. During and after drilling a well, there are a number of ways of detecting whether rocks are currently oil saturated, or have been oil saturated. These include detecting the concentration and composition of gas in drilling fluids using gas chromatography; visual inspection; 'wireline' logging; measuring while drilling (MWD); logging while drilling (LWD) or the like to detect changes in properties of rocks and fluids. Most of these techniques are too expensive or complicated to implement on every exploration well. Also, these methods cannot always detect residual oil, particularly if its concentration is beneath the limit of detection (LoD) of the measuring device. LWD tools and measurements are expensive, and involve adding tools to the drill stem and sending them 'down-hole' to measure characteristics like resistivity, pressure, gamma radiation, density, porosity, water saturation and so on. Testing of this kind is often undertaken before making expensive decisions about well completion. However, a more detailed chemical analysis would aid in the characterisation of the geological formation.

Accordingly, analysis of drilling fluids and rock cuttings is of value during exploration and production of hydrocarbons. At present, drilling fluid (or 'mud') is frequently analysed for dissolved gases in a process known as 'mud gas logging'. Samples are extracted from the returning mud and subsequently analyzed for chemical composition by chromatographic or spectroscopic means such as infrared absorption (IR); gas chromatography (GC); mass spectrometry (MS); or gas chromatography and mass spectrometry (GC-MS).

The use of MS and GC-MS provides richer information about chemical composition, and has permitted studies of carbon isotopes for geochemical purposes. Typically, GC-MS analysis has been carried out using large, expensive and power hungry instruments located in central laboratories often remote from well-sites. The turn-around for analysis of drilling mud and cuttings by GC-MS would be of the order of two to four weeks from sample collection to delivery of a report on chemical composition—often too late to have an impact on drilling decisions with a high opportunity cost such as geo-steering, well testing or well completion.

One disadvantage of commercially available well-site GC and GC-MS technology is that it is limited to detecting low carbon number hydrocarbons (e.g. $C_1$ to $C_5$). Geochemists are increasingly interested in detecting heavier compounds outside the 'bandwidth' of today's mud gas logging instruments. Free organic matter (i.e. Bitumen) in rocks, drilling mud or rock cuttings is a highly complex mixture that contains a rich variety of compounds including alkanes, aliphatics and aromatics. Measuring all of these compounds provides geochemists with valuable information about formation origin, age and thermal maturity. For example, lower molecular weight alkanes (i.e. $<C_{21}$) are derived from algae and bacteria, whereas higher molecular weight homologs (e.g. $C_{22}$-$C_{33}$) are derived from plant waxes. Furthermore, odd-dominate alkanes indicate immature organic matter and a loss of the odd dominance reveals that bitumen is in the oil window. Similarly, aliphatic-rich material is derived from marine shales containing algae remains, whereas more polar matter is derived from land plant remains. Steranes are found in aliphatic fractions and were once components of cell membranes. Steranes are source specific: $C_{27}$ steranes are produced by algae; $C_{29}$ steranes are produced by land plants and $C_{28}$ steranes are prevalent in lacustrine (i.e. fresh water) environments. The ratio of $C_{28}$ steranes to $C_{29}$ steranes is used as an age indicator, and the prevalence of the 20S over the 20R sterane isomers gives an indication of thermal maturity. Likewise, hopanes are found in aliphatic fractions and prevalence of the 22S over the 22R isomer gives an indication of thermal maturity.

Detecting these substances and measuring their relative concentrations and other characteristics is important during exploration and production in order to identify source rocks in a formation and determine whether or not they bear materials that may be in the 'oil window'. Today, the analytical tools with sufficient performance to resolve and identify 'marker' compounds from aromatic, aliphatic and polar fractions are only available in central laboratories. Due to their large size, weight and infrastructure overhead it would not be feasible to deploy them at the well-site. Accordingly there is a need for an improved, portable analytical tool.

SUMMARY OF THE INVENTION

These and other problems are addressed by the present invention in providing a portable analytical system and a method for using this system for the analysis of samples extracted from drilling fluid. The portable analytical solution may be deployed topside at the well-site and used to perform detailed real-time analysis of formation fluids and extracts of rock cuttings which pass to the surface from a drilling tool. Such a system provides response rates that are sufficiently rapid so as to quickly and effectively separate the chemical constituents from a sample containing drilling fluids or rock cutting extracts, and sufficiently selective so as to permit easy identification of chemical species of interest based on their molecular ions and without the need for spectral interpretation.

The invention provides a method for analysing samples extracted from drilling fluids, and rock cuttings, at the well-site in order to rapidly determine their chemical composition and the concentrations of the formation fluids and rock extracts of interest in the sample mixture. The method described could be used during oil and gas exploration and production to determine whether the drill stem has passed through a hydrocarbon-bearing region, or rocks that are capable of functioning as an oil reservoir or that may have been a source rock, or that may have come into contact with oil, or that may contain oil at present.

In one embodiment of a method provided in accordance with the present teaching, a portable analytical system is provided that may be utilised at a well-site for the analysis of drilling fluids as they are collected from the well-head. It will be understood that the drilling fluid is a complex heterogeneous mixture containing formation fluids, dissolved gases, water, drilling contaminants, rock cuttings, particulates and drilling mud or drilling lubricants. In accordance with the present teaching, a sample is taken from the drilling fluids and filtered to remove particulates and cuttings, and the remaining fluid sample is made-up into a solution using a solvent or some combination of solvents such as water, dichloromethane or methanol etc. The sample solution may then be injected into the injection port of a portable analytical system. The sample solution is separated into its constituent chemical species by a chromatography system and these species are ionised by a soft ionisation source before being analysed and identified by means of a mass spectrometer detector.

In one mode of operating the method of the invention, a portable analytical system is provided at a well-site for the analysis of rock cuttings as they are collected from the well-head. In the method provided a sample is taken from the drilling fluids and filtered to isolate particulates and cuttings, separating them from the drilling mud dissolved gases, water and other formation fluids. The remaining particulates and rock cuttings are immersed in a solvent or a combination of solvents. The solvent is used to wash the rock cuttings and to extract residual fluids from within the rock cuttings. The resulting sample solution is then injected into the injection port of a portable analytical system. The sample solution is separated into its constituent chemical species by a chromatography system and these species are ionised by a soft ionisation source before being analysed and identified by means of a mass spectrometer detector.

In another embodiment of the method a fluid sample is taken from the drilling fluids at the well-site. The fluid sample is filtered and cleaned-up before being made-up into a solution using a solvent or some combination of solvents. The resulting fluid sample solution is then injected into a portable analytical system provided at the well-site. A chromatography system then separates the fluid mixture into its constituent chemical species and these species are ionised by a soft ionisation source before being analysed and identified by means of a mass spectrometer detector.

In another embodiment of the method a portable analytical system is provided at a well-site for the analysis of drilling fluids as they are collected from the well-head, wherein the portable analytical system includes a sample injector, a sample loop, a chromatographic separator, a soft ionisation source and a mass spectrometer detector. In this embodiment of the method a fluid sample is filtered and cleaned-up before being made-up into a solution using a solvent or some combination of solvents. The resulting fluid sample solution is then injected into the injector port, and a sample loop passes the sample through a pre-concentrator. The pre-concentrator collects and purifies the chemical species of interest in a sorbent trap which has the effect of concentrating them before a chromatography system then separates the solution mixture into its constituent chemical species and these species are ionised by a soft ionisation source before being analysed and identified by means of a mass spectrometer detector.

In another embodiment of the method a portable analytical system is provided at a well-site for the analysis of drilling fluids as they are collected from the well-head, wherein the portable analytical system includes a chromatographic separator and a mass spectrometer detector, and wherein the mass spectrometer includes a soft ionisation source, a vacuum interface, a mass analyser and an ion counter. The mass spectrometer is coupled to the chromatographic separator by a soft ionisation source which ionises the chemical species as it elutes from the chromatographic column and the ions are transmitted into a mass analyser inside a vacuum chamber. Ions are filtered by their mass to charge ratios in mass analyser and counted by the ion counter. A computer processes the signal from the ion counter and it is displayed as a mass spectrum on an analytical display.

In another embodiment of the method a portable analytical system is provided at a well-site for the analysis of drilling fluids as they are collected from the well-head, wherein the portable analytical system includes a chromatographic separator and a mass spectrometer detector, and wherein the mass spectrometer includes a soft ionisation source, an ion mobility drift tube, a vacuum interface, a mass analyser and an ion counter. The mass spectrometer is coupled to the chromatographic separator by a soft ionisation source which ionises the chemical species as it elutes from the chromatographic column and the ions are transmitted into an ion mobility drift tube and from there into mass analyser inside a vacuum chamber. Ions are separated by their drift time inside the ion mobility cell and then transmitted through the vacuum interface and into a mass analyser to be filtered by their mass to charge ratios and counted by the ion counter. A computer processes the signal from the ion counter and it is displayed as a mass spectrum on an analytical display.

In another embodiment of the invention a portable analytical system is provided, wherein the portable analytical system includes a sample injector, a sample loop, a GC column coupled to an atmospheric pressure ionisation source, an atmospheric pressure vacuum interface and a mass spectrometer detector. In this embodiment of the method a fluid sample is filtered and cleaned-up before being made-up into a solution using a solvent or some combination of solvents. The resulting fluid sample solution is then injected into the injector port, and a sample loop introduces the sample to the GC column. In a preferred embodiment the chromatographic separator is a GC column, but the chromatographic separator may also be a liquid chromatography (LC) system, supercritical fluid chromatography (SFC) system or a capillary electrophoresis (CE) system. The GC column rapidly separates the sample mixture and elutes its components into an atmospheric pressure ionisation source. Atmospheric ionisation sources typically employ soft ionisation techniques that generate a molecular ion permitting easy interpretation of spectra, limiting fragmentation and easing identification of chemical species particularly when more than one compound elutes simultaneously from the chromatographic column. In a preferred embodiment the atmospheric pressure ionisation source is an electrospray ionisation (ESI) source, but atmospheric ionisation sources are not limited to ESI and include nanospray ionisation, APCI, APPI, DART, DESI, Low temperature plasma ionisation (LTP), APGDI, APCDI and SESI. The ions generated by the atmospheric ionisation source are transmitted into the vacuum chamber by an atmospheric pressure interface before being analysed and identified by means of a mass spectrometer detector.

These and other features and benefit will be understood with reference to the following exemplary embodiments.

DETAILED DESCRIPTION

Figure 1:
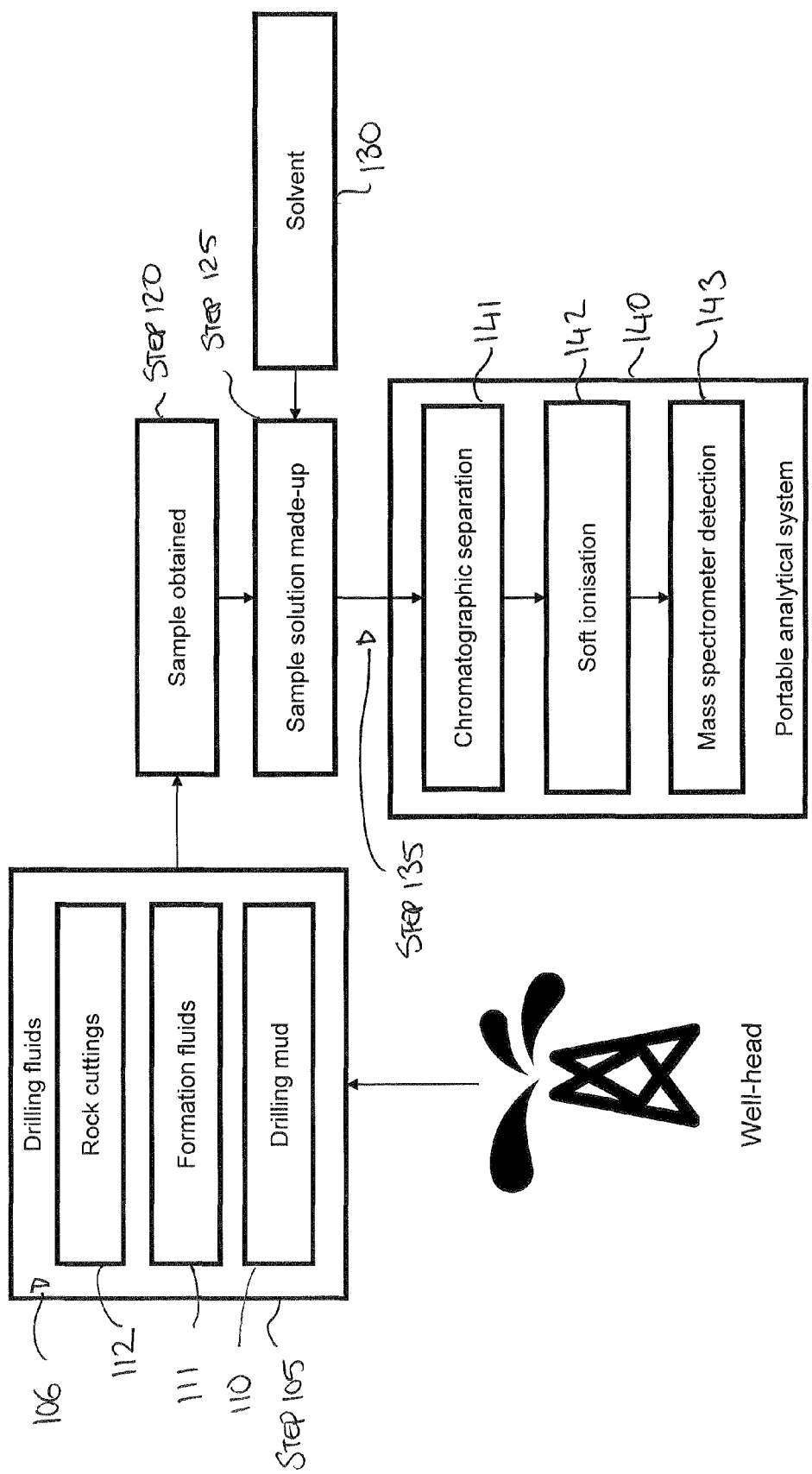
FIG. 1 is a schematic methodology that may be employed in accordance with the present teaching for using a portable analytical system for the analysis of drilling fluids at a well-site. The portable analytical system includes a chromatographic separator, a soft ionisation source and a mass spectrometer detector.

A detailed description of preferred exemplary embodiments of the invention is provided with reference to FIGS. 1 to 10.

It will be appreciated that drilling extracts and crude oil are 'messy' samples. Due to the complex chemical matrix that is a drilling fluid sample, or a bitumen sample extracted from a drilling cutting, lengthy chromatographic separation times are required to ensure adequate separation and purification of all the compounds in the mixture. Gas chromatographic (GC) retention times of the order of hours may be required before all the components of have eluted from the GC column. In fact, samples of interest may contain tens of thousands of components. While users may not need to separate and identify all of the components during drilling, nonetheless an analytical solution will need to rapidly separate and analyse complex samples and identify their components. In the context of modern-day drilling operations, where drilling speeds of hundreds of meters/feet per minute and operating costs of hundreds of thousands of dollars a day are common, the cost of delays and missed opportunities is very high. To address these problems there is provided in accordance with the present teaching, a portable analytical tool and methodology that provides rapid response times. To achieve this improved response rate, the tool advantageously employs a chromatographic solution featuring a faster flow rate and shorter separation times than heretofore possible in drilling mud analysis. By providing for ionisation of the sample in non-vacuum conditions, then the gas chromatographic (GC) flow rate is not limited by the pumping speed of the vacuum pumps and the GC column may have a higher flow rate permitting more rapid separation and a shorter system response time.

It will be appreciated that traditionally where a chromatographic column is used to separate a mixture, a mass spectrometer (MS) detector is used to identify the compounds as they elute. The MS detector is a vacuum instrument and generally features an ion source inside the vacuum chamber to which the GC column is coupled and which ionises molecules of each constituent compound as they elute from the column. Typical ion sources used with GC are electron ionisation (EI) and chemical ionisation (CI). Both EI and CI take place inside the vacuum chamber and involve bombarding eluted molecules with energetic electrons or ions, fragmenting the neutral molecules and producing charged particles (i.e. ions). This fragmentation adds further complexity where some many chemicals are concerned, leading to mass spectral interpretation and further delays. Problems arise when component co-elute from the column and fragments over-lap. Over lapping fragments can make it impossible to separate mass spectra and identify compounds. Co-eluting compounds will be a problem when separations are accelerated by increasing flow rate or temperature ramp for example. To address these shortcomings of previous systems, a system in accordance with the present teaching employs a 'soft' ionisation source that does not fragment chemical species but which instead produces one 'molecular ion', whose mass to charge ratio corresponds to it molecular weight and is a faster and easier means of identifying eluted compounds. The use of soft ionisation permits identification of compounds during rapid separation of compounds. Such a 'soft' ionisation processes may be conducted outside the GC vacuum chamber at elevated pressures and include those provided by techniques such as atmospheric pressure glow discharge ionisation (APGDI), atmospheric pressure corona discharge ionisation (APCDI), atmospheric pressure chemical ionisation (APCI), electrospray ionisation (ESI), atmospheric pressure photo ionisation (APPI), desorption electrospray ionisation (DESI), secondary electrospray ionisation (SESI) and so on.

FIG. 1 shows a method 100 of using such a portable analytical system for the analysis of drilling fluids at a well-site. As will be appreciated by those of ordinary skill in the art, during drilling, drilling fluid samples are taken periodically from a well (Step 105). The drilling fluid sample 106 is a complex mixture that may contain drilling mud 110, formation fluids 111, rock cuttings 112 and other particulates, water and other drilling contaminants and lubricants. In accordance with the present teaching, the drilling fluid sample is filtered (Step 120) and made-up into a solution (Step 125) using a solvent (130). The sample solution is injected (Step 135) into a portable analytical system 140 which is provided topside of the well and incorporates a chromatographic separator 141, a soft ionisation source 142 and a mass spectrometer detector 143. The sample mixture is separated by a chromatography column so that its component species elute individually into a soft ionisation source which generates molecular ions that are analysed and identified by a mass spectrometer detector.

Figure 2:
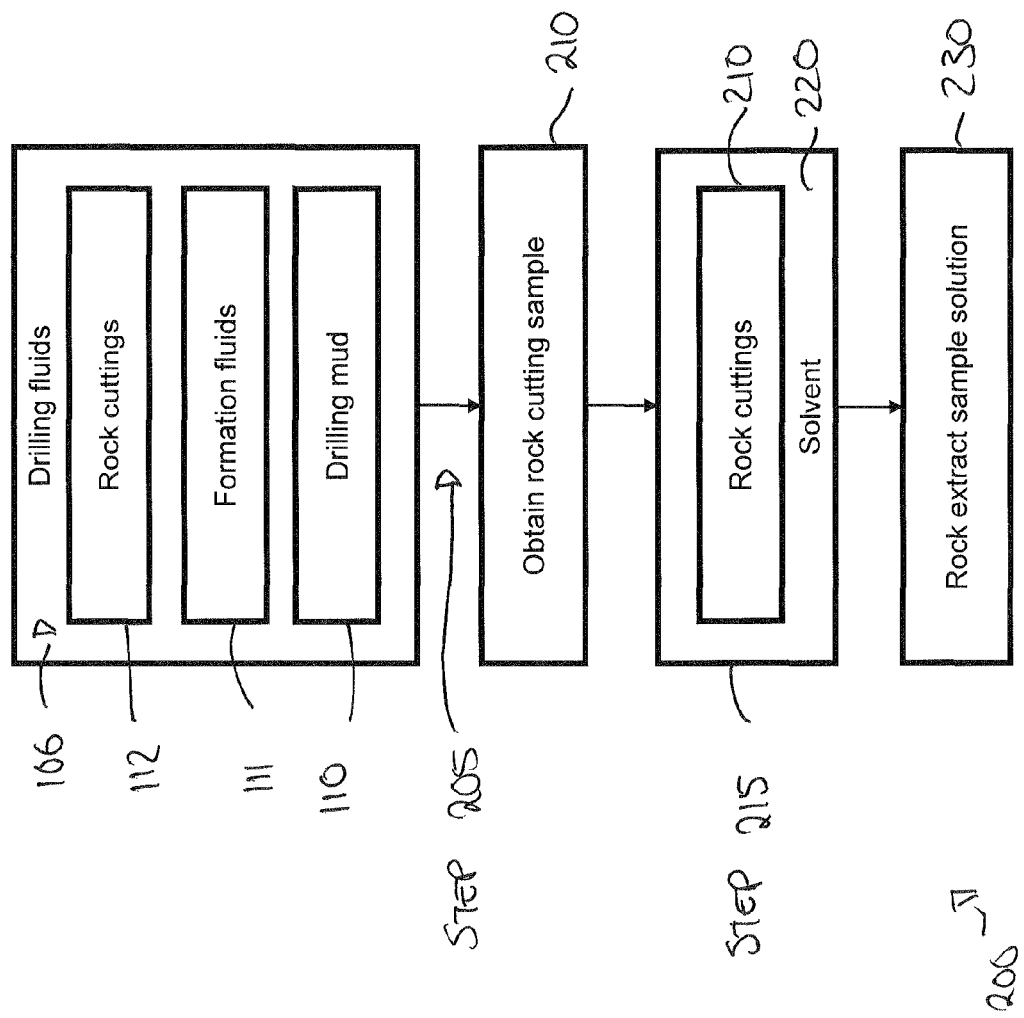
FIG. 2 shows a method for preparing samples for analysis by obtaining rock cuttings from drilling fluids and extracting a sample solution from rock cuttings using a solvent prior to injection in a portable analytical system.

FIG. 2 describes a method 200 for preparing a sample from extracts from rock cuttings for analysis by a portable analytical system. The same reference numerals will be used for similar components. A drilling fluid sample is taken from drilling fluid 106 at a well-site. The sample is filtered (Step 205) and rock cuttings and particulates are separated from drilling mud, water and dilute formation fluids to provide a rock cutting sample 210. The remaining particulates and rock cuttings are immersed in a solvent or a combination of solvents 220, (Step 215). The solvent is used to wash the rock cuttings and to extract residual oil and formation fluids 230 from within the rock cuttings. In a preferred embodiment of the method the solvent is dichloromethane, but solvents include and are not limited to water, methanol, formic acid and acetonitrile. This resulting rock extract sample solution may then be injected into the injection port of a portable analytical system for analysis and identification of aromatic, aliphatic and polar fractions.

Figure 3:
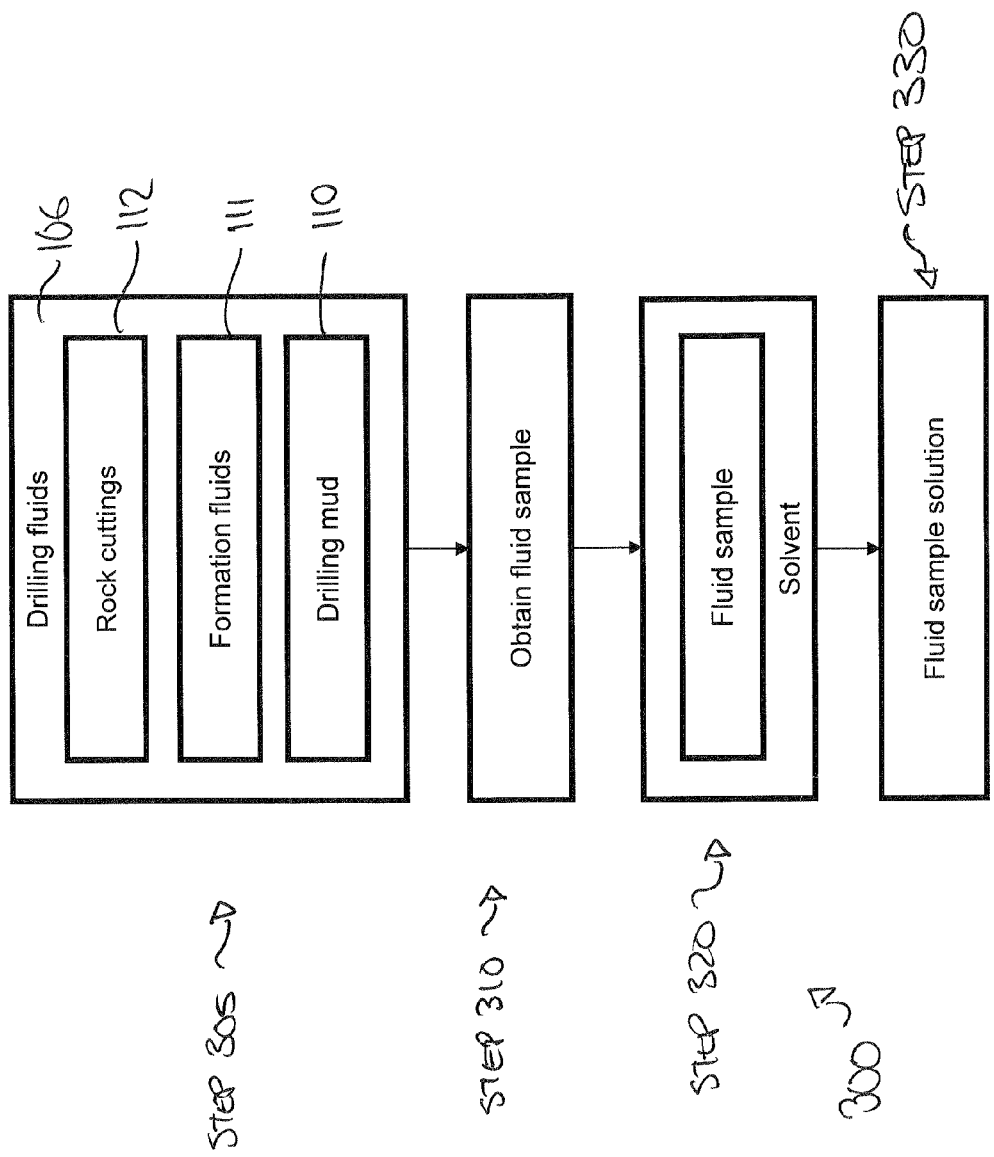
FIG. 3 shows a method for preparing samples for analysis by obtaining fluid samples from drilling fluids and making up a sample solution from a fluid sample using a solvent prior to injection in a portable analytical system.

FIG. 3 describes a method 300 for preparing a sample from formation fluids for analysis by a portable analytical system. A sample is taken from drilling fluid at a well-site (Step 305). The sample is filtered and rock cuttings and particulates are separated from drilling mud, water and dilute formation fluids to obtain a fluid sample (Step 310). The fluid sample is then diluted in a solvent or a combination of solvents. The solvent is used to dissolve fluids and to make-up a solution containing drilling mud, water, formation fluids and other impurities from the drilling fluid. In a preferred embodiment of the method the solvent is toluene, but solvents include and are not limited to dichloromethane, water, methanol, formic acid and acetonitrile. The resulting fluid sample solution may then be injected into the injection port of a portable analytical system for analysis and identification of aromatic, aliphatic and polar fractions (Step 330).

Figure 4:
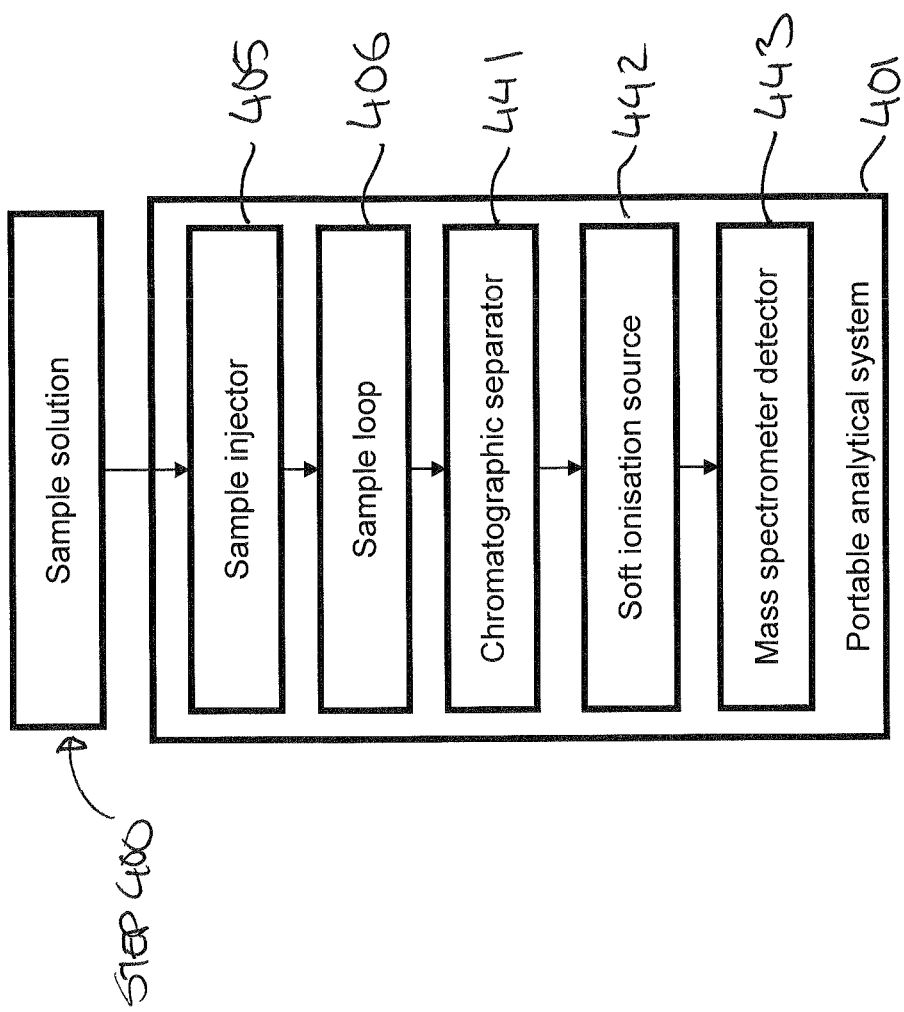
FIG. 4 is a diagram of a portable analytical system for the analysis of fluids on-site. The portable analytical system includes a sample injector, a sample loop, a chromatographic separator, a soft ionisation source and a mass spectrometer detector.

FIG. 4 describes an exemplary analytical methodology that may be employed. A sample solution is introduced into a sample injection port of a portable analytical system as provided in accordance with the present teaching (Step 400). The system 401 comprises a sample injector 405 provided in fluid communication with a sample loop 406, in fluid communication with a chromatographic separator 441, a soft ionisation source 442 and a mass spectrometer 443. The sample is loaded into the chromatography column 441 by means of the sample loop 406. The sample mixture is separated into its individual components by means of the chromatography column 441 before they are sequentially ionised by the soft ionisation source 442 as they elute from the column. The soft ionisation source generates molecular ions for each of the constituents of the sample mixture. These ions are transported into the mass spectrometer system 443 where they are filtered by their mass to charge ratios and identified by their mass spectra and molecular ion peaks.

Figure 5:
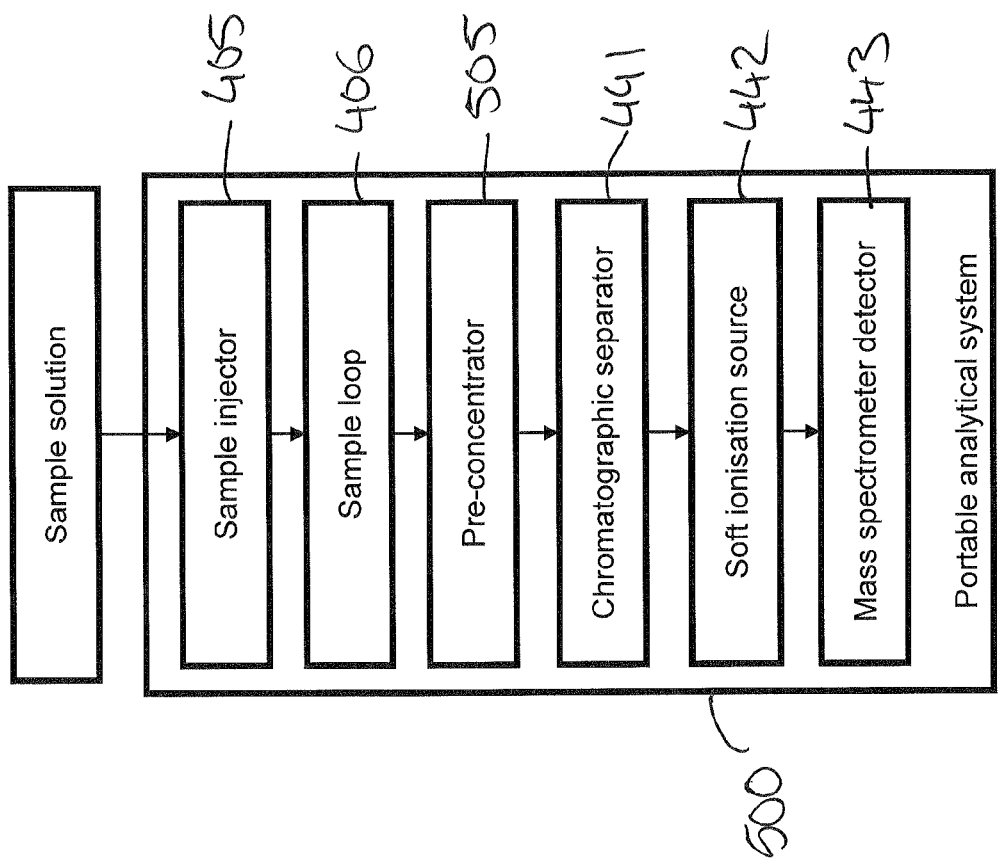
FIG. 5 is a diagram of a portable analytical system for the analysis of fluids on-site. The portable analytical system includes a sample injector, a sample loop, a pre-concentrator, a chromatographic separator, a soft ionisation source and a mass spectrometer detector.

FIG. 5 describes in schematic form another system 500 in accordance with the present teaching, modified relative to the system of FIG. 4. In this arrangement, a sample solution is introduced into the sample injection port 405. Again, the sample is loaded onto a chromatography column 441 by means of a sample loop. The sample loop includes a pre-concentrator 505 that collects the species of interest by means of for example a sorbent trap before they are loaded onto a chromatography column. The pre-concentrator 505 purifies the chemical species of interest in which has the effect of concentrating them into a small injection volume before the mixture is injected onto the column 441 and separated into its individual components by means of chromatography. The components of the mixture are sequentially ionised by a soft ionisation source 442 as they elute from the column. The soft ionisation source 442 generates molecular ions for each of the constituents of the sample mixture. These ions are transported into a mass spectrometer system 443 where they are filtered by their mass to charge ratios and identified by their mass spectra and molecular ion peaks.

Figure 6:
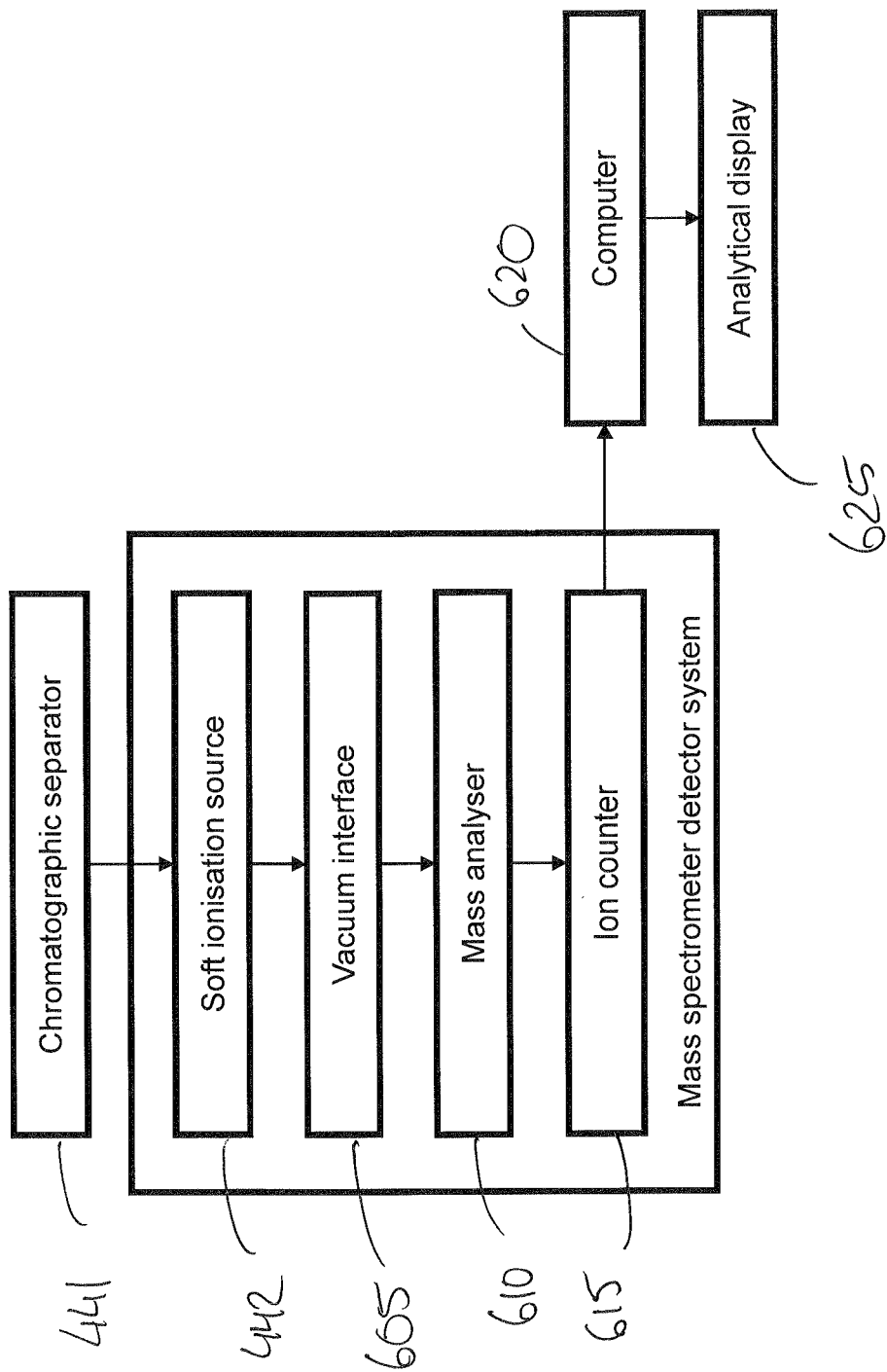
FIG. 6 is a diagram of a mass spectrometer system for use in a portable analytical system for the on-site analysis of fluids. The mass spectrometer detector system includes a soft ionisation source, a vacuum interface, a mass analyser and an ion counter, a computer and an analytical display. The soft ionisation source of the mass spectrometer detector system is coupled to a chromatographic separator.

FIG. 6 shows a further arrangement of a portable analytical system in accordance with the present teaching. A soft ionisation source 442 is coupled with a chromatography column 441 and employed to generate molecular ions from eluent from the column. A vacuum interface 605 is used to transport ions from outside the mass spectrometer's vacuum chamber to inside that vacuum chamber where they are filtered by a mass analyser 610 and counted by an ion detector 615. As will be understood by those skilled in the art, ions are filtered by their mass to charge ratios in the analyser and impact the ion counter generating an electrical current. This current is a signal that may be amplified and filtered by ion counter electronics and processed by a computer 620 before being displayed as chromatograms and mass spectra in an analytical software application 625.

Figure 7:
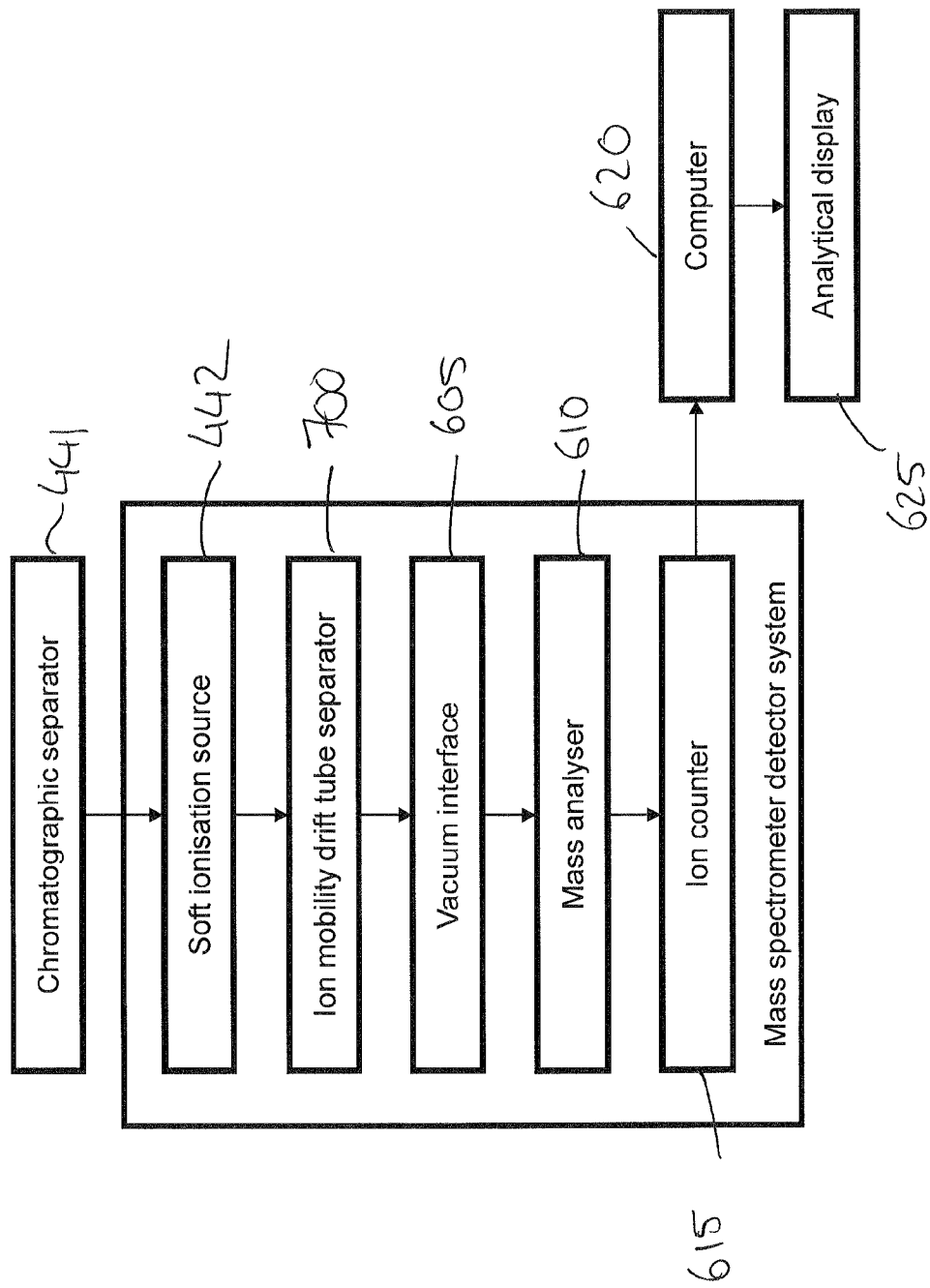
FIG. 7 is a diagram of a mass spectrometer system for use in a portable analytical system for the on-site analysis of fluids. The mass spectrometer detector system includes a soft ionisation source, an ion mobility drift tube separator, a vacuum interface, a mass analyser and an ion counter, a computer and an analytical display. The soft ionisation source of the mass spectrometer detector system is coupled to a chromatographic separator.

FIG. 7 is a diagram showing an alternative arrangement to that described with reference to FIG. 6. In this embodiment the mass spectrometer system includes a soft ionisation source 442, coupled to a chromatography column 441, which ionises the eluent. By providing an ion mobility drift tube separator 700 it is possible to provide for further separating ionised species in order of their drift time. This separator or ion mobility cell is desirably provided between the ionisation source 442 and the vacuum interface 605. Ion mobility separators function by separating ions by means of mobility in a strong electrostatic field at atmospheric pressure or in a very rough vacuum (i.e. >1 Torr). The ions inside an ion mobility cell will tend to drift due to an electrostatic force applied thereon, but their drift is resisted by collisions with neutral molecules of air or buffer gases. In this way ions are separated by drift time and by drag due to the ions cross sectional area. The use of an ion mobility cell introduces a second dimension of separation in addition to chromatography that is particularly effective when analysing very complex mixtures such as crude oils. The ion mobility drift cell may also be used to separate the ionised isomers of compounds with the same mass to charge ratio by drift time.

Figure 8:
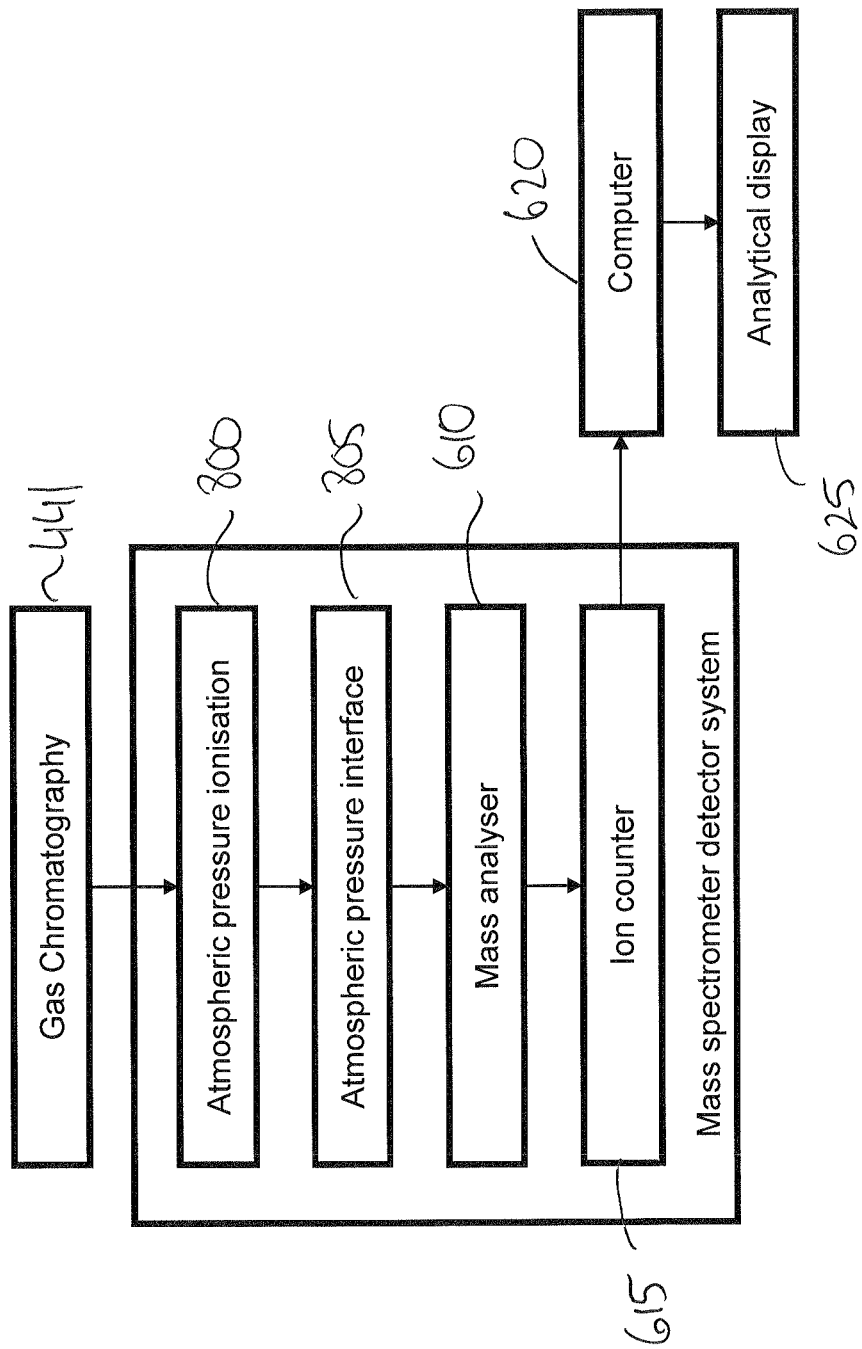
FIG. 8 is a diagram of a mass spectrometer system for use in a portable analytical system for the on-site analysis of fluids. The mass spectrometer detector system includes an atmospheric ionisation source, an atmospheric pressure vacuum interface, a mass analyser and an ion counter, a computer and an analytical display. The atmospheric pressure source of the mass spectrometer detector system is coupled to a gas chromatography column.

FIG. 8 is another arrangement of a portable analytical system provided in accordance with the present teaching. A gas chromatography column 441 is coupled to an atmospheric pressure ionisation source 800 that produces ions by means of soft ionisation. The atmospheric ionisation source is preferably an electrospray ionisation source, such as the exemplary schematic shown in FIG. 9, but includes and is not limited to nanospray ionisation, APCI, APPI, DART, DESI, Low temperature plasma ionisation (LTP), APGDI, APCDI and SESI. The GC column 441 elutes species into the atmospheric ionisation source 800 where they are ionised and transported into a vacuum chamber by means of an atmospheric pressure interface 805. The ions are filtered and analysed by a mass analyser 610. The mass analyser may composed of one or a plurality of the following: quadrupole, ion trap, linear ion trap, time of flight (TOF), triple quadrupole, monopole, Fourier transform (FT), magnetic sector, cross-field, rotating field, orbital ion trap, linear ion trap, rectilinear ion trap or cyloidic. Ions are filtered by their mass to charge ratios in the analyser and impact the ion counter 615 generating an electrical current. This current is a signal that may be amplified and filtered by ion counter electronics and processed by a computer 620 before being displayed as chromatograms and mass spectra in an analytical software application 625.

Figure 9:
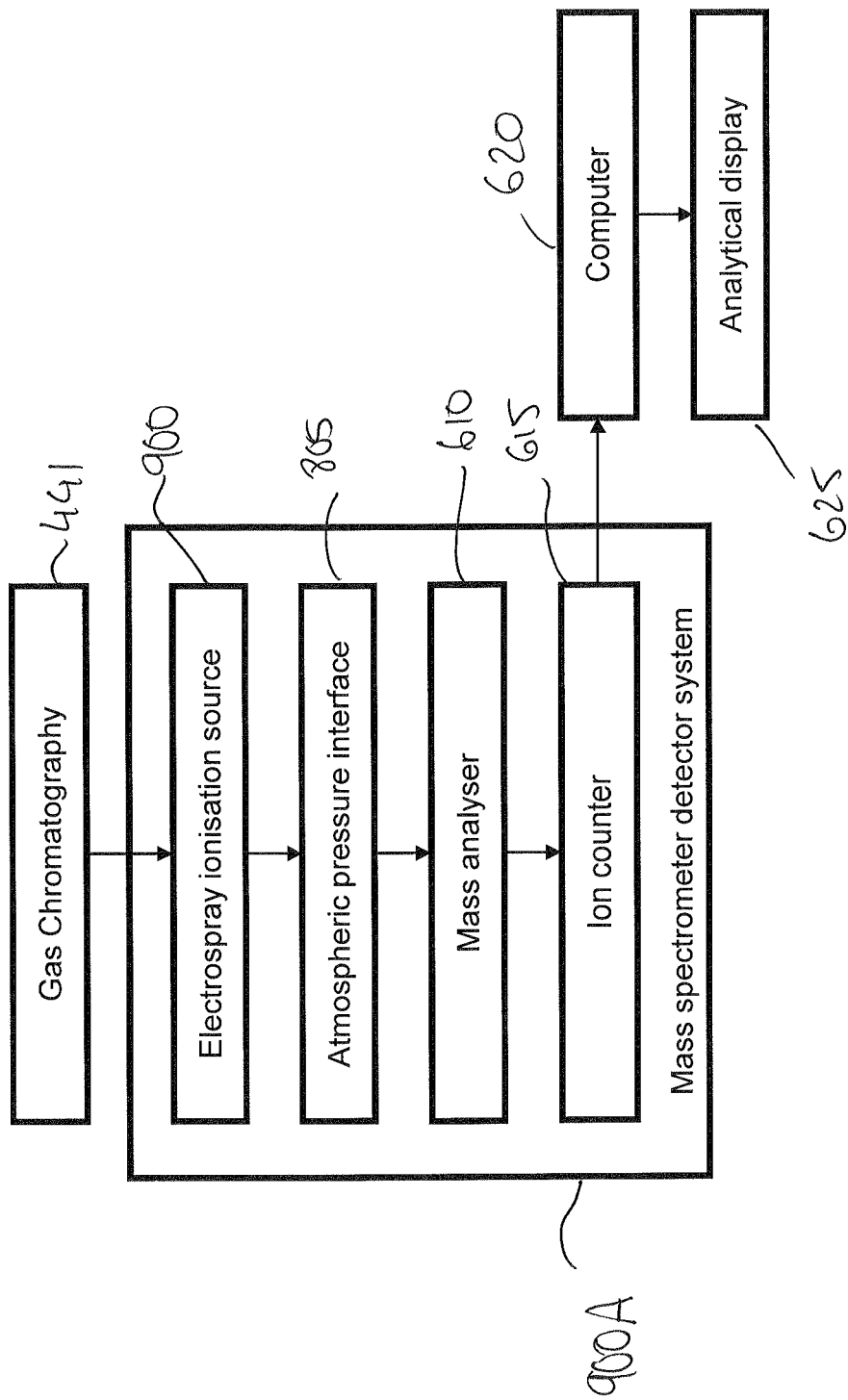
FIG. 9 is a diagram of a preferred embodiment of the mass spectrometer system for use in a portable analytical system for the on-site analysis of fluids. The mass spectrometer detector system includes an electrospray ionisation source, an atmospheric pressure vacuum interface, a mass analyser and an ion counter, a computer and an analytical display. The electrospray ionisation source of the mass spectrometer detector system is coupled to a gas chromatography column.

FIG. 9 is a preferred arrangement of a mass spectrometer system incorporating a mass analyser for use in the portable analytical system of the present invention. The mass spectrometer system 900a is based on atmospheric ionisation and is coupled to a GC column 441 which provides an eluent that is fed to an electrospray ionisation source, (ESI) 900. The GC column elutes species into the ESI source where they are ionised by the charged spray in an efficient process known as secondary electrospray ionisation (SESI).

Figure 10:
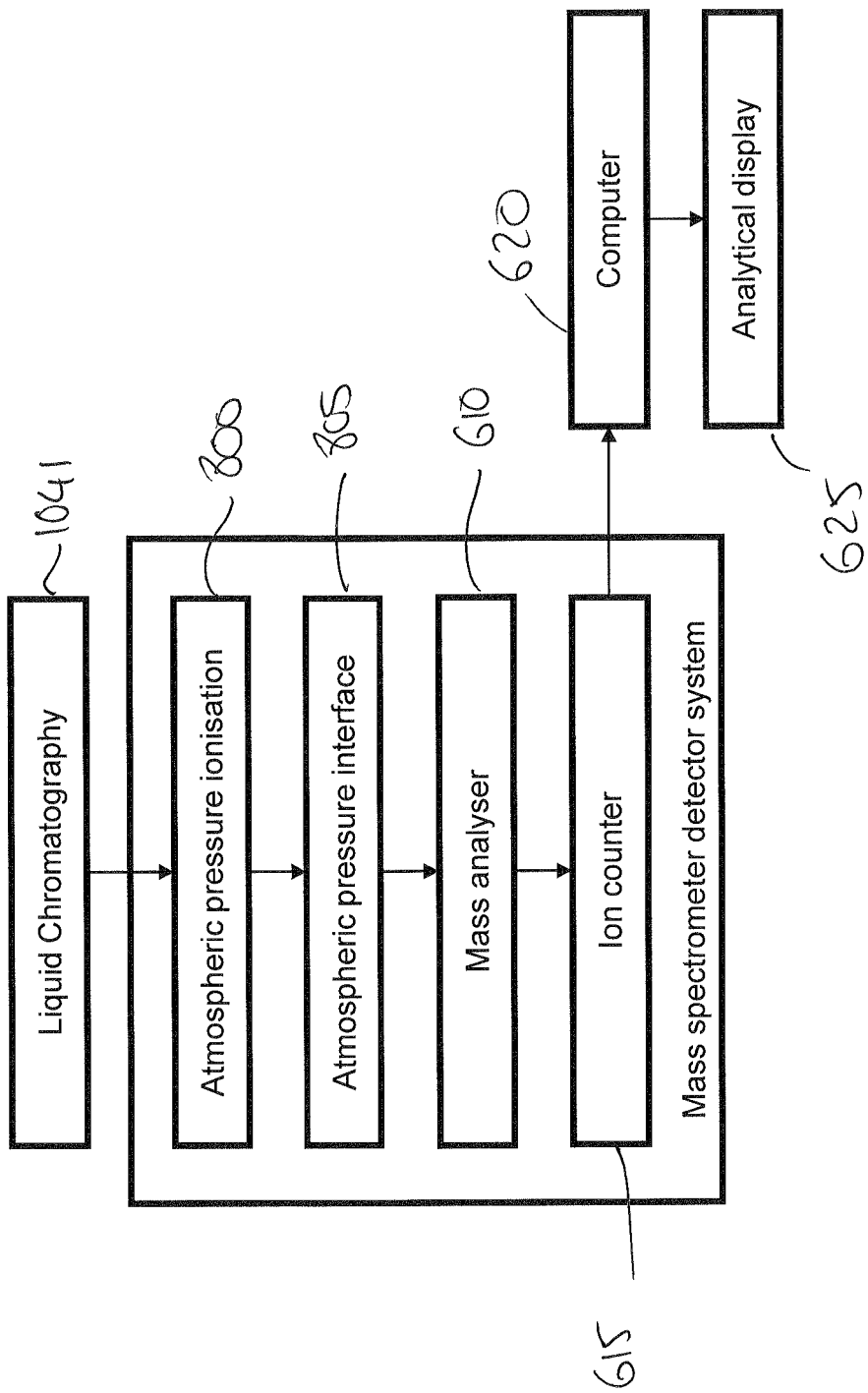
FIG. 10 is a diagram of another embodiment of the mass spectrometer system for use in a portable analytical system for the on-site analysis of fluids. The mass spectrometer detector system includes an atmospheric ionisation source, an atmospheric pressure vacuum interface, a mass analyser and an ion counter, a computer and an analytical display. The atmospheric ionisation source of the mass spectrometer detector system is coupled to a liquid chromatography column.

FIG. 10 shows an alternative arrangement that may be employed in accordance with the teaching of the present invention. In FIG. 10 the GC column heretofore described is replaced with a liquid chromatography (LC) column 1041 that is coupled to an atmospheric ionisation source 800 which may be implemented using an electrospray ionisation source as was described with reference to FIG. 9. LC is particularly effective when analysing thermally labile, polar or in-volatile species of interest. In a further modification the LC column could be replaced with a supercritical fluid (SFC) chromatography column. SFC is an analytical technique that utilises a supercritical fluid such as $CO_2$ which is supercritical above its triple point pressure and temperature. SFC is highly versatile because it is capable of dissolving and separating both volatile and involatile compounds, as well as polar and non-polar molecules. A further advantage of SFC is that is generates no solvent waste since supercritical fluids such as $CO_2$ simply evaporate or are recycled into the chromatography system. SFC is also particularly effective when coupled with an atmospheric pressure, soft ionisation source such as ESI. This embodiment may be particularly valuable when wishing to rapidly analyse samples extracted from formation fluids or rock cuttings for the composition and concentrations of all fractions including aromatic, aliphatic and polar. Information derived from the compositions of fractions can be used to understand the origins of the fluids in terms of plant, algae or lacustrine matter, and in terms of their age and thermal maturity. This geochemical data may be used during drilling to determine if the drill string has passed through rock that is in the 'oil window', or through other hydrocarbon bearing rocks or source rocks.

It will be appreciated and understood that what has been described herein are exemplary arrangements of an analysis tool that is directed towards real-time analysis of drilling fluids which may be generally considered as including any fluid that occurs in the pores of a rock or rock strata. Within the context of drilling an oil or gas well it will be understood that such strata or rocks contain different fluids, such as various saturations of oil, gas and water, and these fluids provide information as to the likelihood of encountering a hydrocarbon reserve. By employing a soft ionisation source such as the exemplary atmospheric ionisation source that effects ionisation of the sample in non-vacuum conditions, the chromatographic flow rate is not limited by the pumping speed of the vacuum pumps and the column may have a higher flow rate permitting more rapid separation and a shorter system response time. Soft ionisation, i.e. the formation of ions without breaking chemical bonds, normally at low energies, is particularly advantageous in the context of the chemically complex samples as described herein in that soft ionisation advantageously produces a 'molecular ion', whose mass to charge ratio or time of flight corresponds to it molecular weight, and has is a faster and easier means of identifying eluted compounds. Soft ionisation is also a low energy ionisation process that does not break chemical bonds and therefore produces few or no molecular fragments, only molecular ions, and therefore reduces chemical noise and interference which considerably simplifies the analysis of complex mixtures such as drilling fluids, natural gas and crude oil. The separation of the fluid into its chemical constituents has been described with reference to the exemplary use of a chromatography column that could be a gas, liquid or supercritical fluid based chromatography module. However it is possible to separate mixtures using other separation techniques such as ion mobility, field assymetic ion mobility spectrometry (FAIMS) or capillary electrophoresis and the use of such techniques should be considered within the context of the separation module described herein.

While the specifics of the mass spectrometer have not been described herein a portable instrument such as that described herein may be advantageously manufactured using microengineered instruments such as those described in one or more of the following co-assigned U.S. applications: U.S. patent application Ser. No. 12/380,002, U.S. patent application Ser. No. 12/220,321, U.S. patent application Ser. No. 12/284,778, U.S. patent application Ser. No. 12/001,796, U.S. patent application Ser. No. 11/810,052, U.S. patent application Ser. No. 11/711,142 the contents of which are incorporated herein by way of reference. Within the context of the present invention the term microengineered or microengineering or microfabricated or microfabrication is intended to define the fabrication of three dimensional structures and devices with dimensions in the order of millimeters or sub-millimeter scale.

Where done at micron-scale, it combines the technologies of microelectronics and micromachining. Microelectronics allows the fabrication of integrated circuits from silicon wafers whereas micromachining is the production of three-dimensional structures, primarily from silicon wafers. This may be achieved by removal of material from the wafer or addition of material on or in the wafer. The attractions of microengineering may be summarised as batch fabrication of devices leading to reduced production costs, miniaturisation resulting in materials savings, miniaturisation resulting in faster response times and reduced device invasiveness. Wide varieties of techniques exist for the microengineering of wafers, and will be well known to the person skilled in the art. The techniques may be divided into those related to the removal of material and those pertaining to the deposition or addition of material to the wafer. Examples of the former include:

Wet chemical etching (anisotropic and isotropic)
Electrochemical or photo assisted electrochemical etching
Dry plasma or reactive ion etching
Ion beam milling
Laser machining
Excimer laser machining
Electrical discharge machining Whereas examples of the latter include:

Evaporation
Thick film deposition
Sputtering
Electroplating
Electroforming
Moulding
Chemical vapour deposition (CVD)
Epitaxy While exemplary arrangements have been described herein to assist in an understanding of the present teaching it will be understood that modifications can be made without departing from the spirit and or scope of the present teaching. To that end it will be understood that the present teaching should be construed as limited only insofar as is deemed necessary in the light of the claims that follow.

Furthermore, the words comprises/comprising when used in this specification are to specify the presence of stated features, integers, steps or components but does not preclude the presence or addition of one or more other features, integers, steps, components or groups thereof.

The invention claimed is:

1. A topside drilling fluid analysis tool for on-site analysis and identification of fluids generated through hydrocarbon exploration or production, the tool comprising: (a) a separation module configured for coupling to a source of fluids as they are collected from a well-head and for separating the generating fluids into its constituent chemical species, the separation module being coupled to (b) an atmospheric pressure soft ionization source coupled to (c) a mass analyzer, and wherein the atmospheric pressure soft ionization source is coupled to the mass analyzer via an interface between vacuum and atmospheric pressure, the mass analyzer is configured to identify chemical components of the drilling fluid by their molecular ions as they are eluted by the separation module and ionized by the soft ionization source, and wherein the soft ionization source is configured to effect the formation of ions without breaking chemical bonds.

2. The tool of claim 1 wherein the mass analyzer is a microengineered mass analyzer.

3. The tool of claim 1 wherein the mass analyzer is coupled to an ion counter such that ions are operably filtered by their mass to charge ratios in the mass analyzer and impact the ion counter generating an electrical current.

4. The tool of claim 1 wherein the mass analyzer is coupled to an ion counter such that ions are operably filtered by their time of flight in the mass analyzer, and impact the ion counter generating an electrical current.

5. The tool of claim 1 wherein the ionization source is based on a corona discharge.

6. The tool of claim 1 wherein the ionization source is an electrospray ionization source.

7. The tool of claim 1 comprising a sample injector configured for receiving a fluid sample for analysis thereof.

8. The tool of claim 7 comprising a sample loop coupled to the sample injector, the sample loop operably providing for a pre-concentration of a species of interest prior to discharge to the separation module.

9. The tool of claim 8 wherein the sample loop comprises a sorbent trap.

10. The tool of claim 1 wherein the separation module is configured to separate the fluid through chromatography.

11. The tool of claim 10 wherein the separation modules comprises one of a gas chromatography column, a liquid chromatographic column or a supercritical fluid chromatographic column.

12. The tool of claim 1 wherein the separation module operably separates the fluid through ion mobility, field asymmetric ion mobility or capillary electrophoresis.

13. A method of analyzing drilling fluids resultant from hydrocarbon exploration and production, the method comprising at a topside of a hydrocarbon exploration or production well: (a) providing a separation module; (b) providing an atmospheric pressure soft ionization source; (c) providing a mass analyzer; and, (d) introducing a fluid sample derived from the drilling fluid into the separation module so as to separate the sample into its individual components, using the ionization source to effect an ionization of the separation module eluent and providing for filtering of the resulting ions based on their charge to mass or time of flight using the mass analyzer, wherein the soft ionization source is configured to effect the formation of ions without breaking chemical bond.

14. The method of claim 13 comprising prior to introduction of the fluid sample into the separation module;
  a. taking a sample from drilling fluid topside at a well-site;
  b. filtering the sample to separate rock cuttings and particulates from drilling mud, water and dilute formation fluids to obtain a concentrated fluid sample;
  c. making up a solution of the fluid sample in a solvent or a combination of solvents; and,
  d. introducing the solution through a sample interface into the separation module.

* * * * *